(12) United States Patent
Skinner et al.

(10) Patent No.: US 9,731,004 B2
(45) Date of Patent: Aug. 15, 2017

(54) PROCESS FOR PREPARING VACCINE COMPOSITION

(75) Inventors: Murray Skinner, Worthing West Sussex (GB); Simon Hewings, Worthing West Sussex (GB); Duncan Packer, Worthing West Sussex (GB); Richard Poland, Worthing West Sussex (GB)

(73) Assignee: Allergy Therapeutics (UK) Limited, Worthing West Sussex (GB)

( * ) Notice: Subject to any disclaimer, the term of this patent is extended or adjusted under 35 U.S.C. 154(b) by 0 days.

(21) Appl. No.: 14/112,544

(22) PCT Filed: Apr. 20, 2012

(86) PCT No.: PCT/GB2012/050883
§ 371 (c)(1),
(2), (4) Date: Jan. 5, 2014

(87) PCT Pub. No.: WO2012/143732
PCT Pub. Date: Oct. 26, 2012

(65) Prior Publication Data
US 2014/0106455 A1    Apr. 17, 2014

(30) Foreign Application Priority Data
Apr. 21, 2011 (GB) .................................. 1106802.0

(51) Int. Cl.
| | |
|---|---|
| *A23J 1/00* | (2006.01) |
| *A61K 38/00* | (2006.01) |
| *A61K 39/00* | (2006.01) |
| *A61K 39/35* | (2006.01) |
| *A61K 39/36* | (2006.01) |
| *A61K 39/38* | (2006.01) |
| *A61K 39/385* | (2006.01) |
| *C07K 1/00* | (2006.01) |
| *C07K 14/00* | (2006.01) |
| *C12M 1/00* | (2006.01) |
| *C12M 3/00* | (2006.01) |
| *A61K 9/14* | (2006.01) |

(52) U.S. Cl.
CPC .............. *A61K 39/36* (2013.01); *A61K 9/145* (2013.01); *A61K 2039/55572* (2013.01); *A61K 2039/60* (2013.01); *A61K 2039/622* (2013.01)

(58) Field of Classification Search
None
See application file for complete search history.

(56) References Cited

U.S. PATENT DOCUMENTS

| | | | |
|---|---|---|---|
| 4,070,455 A | 1/1978 | Green et al. | |
| 4,234,569 A | 11/1980 | Marsh | |
| 4,912,094 A | 3/1990 | Myers et al. | |
| 4,987,237 A | 1/1991 | Myers et al. | |
| 7,815,920 B2 | 10/2010 | Wheeler et al. | |
| 2003/0007977 A1 | 1/2003 | Wheeler et al. | |
| 2005/0266011 A1 | 12/2005 | Maa et al. | |
| 2008/0193473 A1 | 8/2008 | Zagury et al. | |

FOREIGN PATENT DOCUMENTS

| | | |
|---|---|---|
| CN | 101972472 A | 2/2011 |
| EP | 0 192 321 | 8/1986 |
| EP | 0 367 306 A2 | 5/1990 |
| EP | 0988862 A2 | 3/2000 |
| EP | 1 537 846 | 6/2005 |
| EP | 1 743 908 | 1/2007 |
| JP | 63-159324 | 7/1988 |
| JP | 06-329553 | 11/1994 |
| JP | 2010-029109 | 2/2010 |
| WO | WO 96/34626 A1 | 11/1996 |
| WO | 98/44947 A1 | 10/1998 |
| WO | WO 04/000444 | 12/2003 |
| WO | WO 2005/052137 A1 | 6/2005 |
| WO | WO 2011/036562 A1 | 3/2011 |

OTHER PUBLICATIONS

The International Search Report for International Application No. PCT/GB2012/050883, mailed Jun. 15, 2012, pp. 1-4.
The Written Opinion of the International Searching Authority for International Application No. PCT/GB2012/050883, mailed Jun. 15, 2012, pp. 1-4.
The International Preliminary Report on Patentability for International Application No. PCT/GB2012/050883, issued Oct. 22, 2013, pp. 1-5.
Ibarrola et al., "Biological characterization of glutaraldehyde-modified Parietaria judaica pollen extacts" Clin Exp Allergy (2004), vol. 34, pp. 303-309 (Blackwell Publishing Ltd.).
Bathurst et al., "An experimental vaccine cocktail for Plasmodium falciparum malaria," Vaccine,11(4):449-56 (1993).
Blum, "Variants of hepatitis B, C and D viruses: molecular biology and clinical significance," Digestion, 56(2):85-95 (1995).
Deprez et al., "Comparative efficiency of simple lipopeptide constructs for in vivo induction of virus-specific CTL," Vaccine, 14(5):375-82 (1996).
Jahrling et al., "Passive immunization of Ebola virus-infected cynomolgus monkeys with immunoglobulin from hyperimmune horses," Arch Virol Suppl., 11:135-40 (1996).
Katkov, "Hepatitis Vaccines," Management of Chronic Liver Diseases, Medical Clinics North America, 80(5):1189-1200 (Sep. 1996).

(Continued)

*Primary Examiner* — Nora Rooney
(74) *Attorney, Agent, or Firm* — McDonnell Boehnen Hulbert & Berghoff LLP

(57) ABSTRACT

A method of preparing a composition comprising one or more antigens adsorbed to an amino acid wherein said method comprises: (i) mixing a solution of one or more antigens with a solution of the amino acid in an aqueous acid whilst neutralizing the mixture of solutions, thereby forming an adsorbate comprising the one or more antigens and the amino acid; (ii) separating the adsorbate into a desired buffer by cross-flow filtration thereby forming said composition; and (iii) recovering said composition; wherein steps (i) to (iii) are performed in a sterile environment and within a closed system.

17 Claims, 14 Drawing Sheets

(56) References Cited

OTHER PUBLICATIONS

Lieberman & Greenberg, "Hepatitis A and B vaccines in children," Adv Pediatr Infect Dis, 11:333-63 (1996).

Mast & Krawczynski, "Hepatitis E: an overview," Annu Rev Med., 47:257-66 (1996).

Pollinex® Modified Ragweek Pollen Allergen Tyrosine Adsorbate Pre-filled syringes, Product Monograph, Allergy Therapeutics (UK) Limited, revised Oct. 31, 2012, pp. 1-25.

Zhang et al., "Oral immunization with the dodecapeptide repeat of the serine-rich Entamoeba histolytica protein (SREHP) fused to the cholera toxin B subunit induces a mucosal and systemic anti-SREHP antibody response," Infect Immun., 63(4):1349-55 (1995).

PROCESS FOR PREPARING VACCINE COMPOSITION

This application is a national stage application under 35 U.S.C. §371 of International Application No. PCT/GB2012/050883, filed Apr. 20, 2012, which claims the benefit of United Kingdom Application No. GB 1106802.0, filed Apr. 21, 2011, the disclosures of each of which are explicitly incorporated by reference herein.

FIELD OF THE INVENTION

The present invention relates to a method for the manufacture of a sterile composition comprising a modified antigen bound to an amino acid.

BACKGROUND TO THE INVENTION

Vaccination is the best known and most successful application of immunological principles to human health. To be introduced and approved, a vaccine must be effective and the efficacy of all vaccines is reviewed from time to time. An effective vaccine must: induce the desired immune response; be stable on storage; and have sufficient immunogenicity. With non-living vaccines, in particular it is often necessary to control the release of the antigen following administration.

The binding of an antigen to a suspended amino acid has been shown to result in the slow release of the antigen following administration, thereby increasing safety whilst optimising efficacy by prolonging exposure. However, the manufacture of formulations comprising such antigens is problematic since the adsorption of the antigen to the amino acid results in undesired chemical by products that need to be removed. Furthermore, the process must be performed under sterile conditions. As the final product is a suspension it cannot be sterilised by filtration and as the active component is biological it cannot be heat sterilised. Accordingly, sterile suspensions are often manufactured by centrifugation within an aseptic suite.

U.S. Pat. No. 4,070,455 describes finely divided micro-particles of tyrosine having a glutaraldehyde treated allergen dispersed therein. The micro-particles are prepared by mixing a solution of tyrosine in a strong aqueous acid with a solution of glutaraldehyde treated ragweed pollen and then neutralising the resultant solution. The micro-fine particles of tyrosine containing the modified allergen are removed by centrifugation.

EP 0988862 describes the formulation of an antigen, a TH-1 inducing adjuvant and a sparingly water soluble amino acid for use in immunisation. The formulation is prepared by mixing a solution of an antigen and the TH1-inducing adjuvant with a solution of the sparingly soluble amino acid or derivative in a strong aqueous acid whilst neutralising the mixture of solutions, thereby co-precipitating the sparingly soluble amino acid and antigen. The resulting precipitate is removed from the solution by centrifugation, reconstituted with fresh buffer and the adjuvant added.

The use of centrifugation to remove the amino acid/antigen precipitate requires a substantial degree of aseptic exposure and a high dependency on operator interaction. The present invention addresses this problem.

SUMMARY OF THE INVENTION

The present invention overcomes the problems of the prior art by the creation of a system that separates the antigen/amino acid adsorbate using cross-flow filtration. The systems adapts steam sterilisable sintered stainless steel filters routinely used in dead end filtration by including them in a custom designed closed circulatory loop system. This allows the antigen/amino acid adsorbate and the chemical by-products to be removed through the filter as new buffer is added to maintain volume and specification.

The technology requirement arose based on the inability to terminally sterilise or, filter modified allergen tyrosine adsorbate (MATA) product which is insoluble and must be manufactured in a sterile facility. In order to assure sterility it was necessary to develop an enclosed clean in place (CIP) steam in place (SIP) system. The enclosed nature of the system meant that the insoluble MATA component had to be maintained suspended in solution during formulation and buffer exchange steps. To achieve this a continuous cross flow filtration system was developed as described here in.

Due to the closed nature and ability to steam sterilise it is possible to site the hardware outside the aseptic suite (though still within controlled production areas). Therefore the present invention has distinct advantages over existing production methods. The method of the invention substantially reduces exposure of the antigen product to the environment by having a closed aseptic system. The method also reduces the need for physical intervention, de-risking the method both from error and microbial contamination.

According to a first aspect of the present invention there is provided a method of preparing a composition comprising one or more antigens adsorbed to an amino acid wherein said method comprises:

(i) mixing a solution of one or more antigens with a solution of the amino acid in an aqueous acid whilst neutralising the mixture of solutions, thereby forming an adsorbate comprising the one or more antigens and the amino acid;

(ii) separating the adsorbate into a buffer by cross-flow filtration thereby forming said composition; and (iii) recovering said composition;

wherein steps (i) to (iii) are performed in a sterile environment and within a closed system.

Preferably the amino acid is a sparingly soluble amino acid.

Preferably the amino acid is tyrosine, tryptophan or a derivative thereof. More preferably, the amino acid is tyrosine.

Preferably, the one or more antigens are modified with glutaraldehyde.

In a particularly preferred embodiment, the one or more antigens are derived from pollen, mite, moulds, bacteria or viruses.

In one embodiment, the method comprises preparing a composition comprising one or more pollen antigens modified with glutaraldehyde and adsorbed to tyrosine comprising:

(i) modifying one or more pollen antigens with glutaraldehyde;

(ii) removing excess glutaraldehyde using cross-flow filtration to form a modified pollen solution;

(iii) mixing the modified pollen solution with a solution of the tyrosine in an aqueous acid whilst neutralising the mixture of solutions, thereby forming an adsorbate comprising the modified pollen and the tyrosine;

(iv) separating the adsorbate into a buffer by cross-flow filtration thereby forming said composition; and (v) recovering said composition;

wherein steps (iii) to (v) are performed in a sterile environment and within a closed system. Preferably steps (iii) to (v)

are performed in an EU GMP Grade 'C'/ISO Class 7 environment. Preferably steps (i) and (ii) are performed in within an EU GMP Grade 'B'/ISO Class 5 environment.

In another embodiment, the method comprises preparing a composition comprising one or more pollen antigens modified with glutaraldehyde and adsorbed to tyrosine wherein said method comprises:

(i) extracting the one or more pollen antigens into solution to foiiu a pollen extract solution;
(ii) filtering the pollen extract solution to remove solids;
(iii) performing cross-flow filtration and isolating the retentate comprising the pollen antigen;
(iv) modifying the one or more pollen antigens with glutaraldehyde;
(v) removing excess glutaraldehyde using cross-flow filtration to form a modified pollen solution;
(vi) sterile filtering the modified pollen solution;
(vii) mixing the modified pollen solution with a solution of tyrosine in an aqueous acid whilst neutralising the mixture of solutions, thereby forming an adsorbate comprising the modified pollen and the tyrosine;
(viii) separating the adsorbate into a buffer by cross-flow filtration thereby forming said composition; and
(ix) recovering said composition wherein steps (vii) to (ix) are performed in a sterile environment and within a closed system. Preferably steps (vii) to (ix) are performed in an EU GMP Grade 'C'/ISO Class 7 environment. Preferably steps (i) to (vi) are performed in within an EU GMP Grade 'B'/ISO Class 5 environment.

The pollen antigen may be, but is not limited to, Bent pollen, Foxtail pollen, Sweet vernal pollen, False oat pollen, Brome pollen, Crested dogstail pollen, Cocksfoot pollen, Fescue pollen, Yorkshire fog pollen, Rye grass pollen, Timothy pollen, Meadow pollen and Cultivated rye pollen.

Preferably, the one or more antigens consist of bent pollen, Foxtail pollen, Sweet vernal pollen, False oat pollen, Brome pollen, Crested dogstail pollen, Cocksfoot pollen, Fescue pollen, Yorkshire fog pollen, Rye grass pollen, Timothy pollen, Meadow pollen and Cultivated rye pollen.

Preferably the pollen extract solution is filtered using a 0.2 µm pore size filter;

Put another way, the composition preferably comprises all of the pollens in the group consisting of Bent pollen, Foxtail pollen, Sweet vernal pollen, False oat pollen, Brome pollen, Crested dogstail pollen, Cocksfoot pollen, Fescue pollen, Yorkshire fog pollen, Rye grass pollen, Timothy pollen, Meadow pollen and Cultivated rye pollen.

Preferably the pollen is extracted into a phenolic buffered saline solution, preferably at pH 6.5 (preferably containing Sodium Chloride, Potassium Di-Hydrogen Phosphate, Disodium Phosphate Dodecahydrate, 80% w/w Liquified Phenol and Water for Injections (WFWat about 2 to about 8° C., more preferably about 5° C.

Preferably the extraction is performed for about 12-30 hours, more preferably about 14 to about 24 hours, more preferably still for about 18 hours.

Preferably the cross-flow filtration used to isolate the retentate and/or to remove excess glutaraldehyde as described herein is performed using a membrane of 5-10 kDa molecular weight cut off. More preferably the membrane has a 10 kDa molecular weight cut off.

Preferably the cross-flow filtration used to separate the adsorbate is performed using a poly-sintered stainless steel filter, more preferably a 5 µm poly-sintered stainless steel filter, preferably with pressure between 1.1-1.3 bar.

The adsorbate comprising the antigen and the amino acid is formed by mixing the antigen with the amino acid in a strong acid, preferably an inorganic acid, preferable hydrochloric acid (HCl), whilst neutralising the mixture, preferably with NaOH. By neutralisation is meant an adjustment of pH to a value within the range 6.5 to 7.5, preferably 6.8 to 7.2. It is desirable that, at no time, or at least no prolonged time, during the neutralisation does the pH move from equilibrium i.e., move outside the pH range 6.5 to 7.5 or more preferably outside the pH range 6.8 to 7.2.

Preferably the strong acid is HCl having a molarity of about 3.5M to about 4.5M, preferably about 3.8M. Preferably the NaOH has a molarity of about 3 to about 3.5, preferably about 3.2M.

Preferably the composition is a vaccine composition.

In a preferred embodiment, the composition is for use as a vaccine and the antigen is one useful in such a vaccine.

In various embodiments, an adjuvant may be added to the composition, such as MPL, 3-DMPL or a derivative or salt thereof.

According to another aspect of the present invention there is provided a composition prepared by the method of the invention.

DETAILED DESCRIPTION

Various preferred features and embodiments of the present invention will now be described by way of non-limiting examples.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA Methods in Enzymology*, Academic Press; and E. M. Shevach and W. Strober, 1992 and periodic supplements, *Current Protocols in Immunology*, John Wiley & Sons, New York, N.Y. Each of these general texts is herein incorporated by reference.

Antigen

The term "antigen" is used to indicate any molecule that can be specifically recognised by the adaptive elements of the immune response, i.e. by B cells or T cells, or both.

The antigen used in the present invention is preferably an immunogen, i.e. an antigen which activates immune cells to generate an immune response against itself.

The antigen may be obtained by recombinant means or peptide synthesis, or from natural sources or extracts and may be derived from any living or non-living organisms.

The antigen may be derived from bacteria, such as, for example anthrax, *campylobacter*, cholera, diphtheria, enterotoxigenic *E. coli*, *giardia*, gonococcus, *Helicobacter pylori*, *Hemophilus influenza* B, *Hemophilus influenza* non-typable, meningococcus, pertussis, pneumococcus, *salmonella*, *shigella*, *Streptococcus* B, group A *Streptococcus*, tetanus, *Vibrio cholerae, yersinia, Staphylococcus, Pseudomonas* species and *Clostridia* species.

Alternatively, the antigen may be derived from viruses, such as, for example adenovirus, dengue serotypes 1 to 4, ebola (Jahrling et al., Arch Virol Suppl, 11:135-140, 1996), enterovirus, hepatitis serotypes A to E (Blum, Digestion 56:85-95, 1995; Katkov, Med Clin North Am 80:189-200, 1996; Lieberman and Greenberg, Adv Pediatr Infect Dis 11:333-3631996; Mast et al., Annu Rev Med 47:257-266, 1996) herpes simplex virus 1 or 2, human immunodeficiency virus (Deprez et al., Vaccine 14:375-382, 1996), influenza, Japanese equine encephalitis, measles, Norwalk, papilloma virus, parvovirus B19, polio, rabies, rotavirus, rubella, rubeola, vaccinia, vaccinia constructs containing genes coding for other antigens such as malaria antigens, varicella, and yellow fever. Parasites include, for example: *Entamoeba histolytica* (Zhang et al., Infect Immun 63:1349-1355); *Plasmodium* (Bathurst et al., Vaccine 11:449-456, 1993), Toxoplasmosis, and the Helminths.

In a preferred embodiment the antigen is an allergen. The term "allergen" is used to describe an antigen that elicits an unwanted immune hypersensitivity or allergic reaction. An allergy is a hypersensitivity response to an environmental antigen (allergen).

The allergen used in the present invention may be derived from any allergy causing substance, such as, but not limited, to pollen (e.g. Bent pollen, Foxtail pollen, Sweet vernal pollen, False oat pollen, Brome pollen, Crested dogstail pollen, Cocksfoot pollen, Fescue pollen, Yorkshire fog pollen, Rye grass pollen, Timothy pollen, Meadow pollen, Cultivated rye pollen, Ragweed pollen, Mugwort pollen, Birch pollen, Alder pollen, Hazel pollen, Olive pollen, Pariateria pollen, Maple (*Acer negundo*) pollen, Cypress pollen and Japanese Cedar (*Cryptomeria japonica*) pollen, food, insect venom, mould and animal derived material such as animal fur or mites such as the house dust mites (e.g., *D. farinae* or *D. pteronyssinus* or *Blomia tropicalis*).

Preferably the antigen used in the present invention is a pollen antigen. Preferably the pollen antigens are Bent pollen, Foxtail pollen, Sweet vernal pollen, False oat pollen, Brome pollen, Crested dogstail pollen, Cocksfoot pollen, Fescue pollen, Yorkshire fog pollen, Rye grass pollen, Timothy pollen, Meadow pollen and Cultivated rye pollen.

The antigen may be chemically modified by reaction with known substances, for example, but not limited to formaldehyde or glutaraldehyde, preferably glutaraldehyde, which retain or enhance the desired immunogenic properties of the antigen whilst helping to avoid unwanted adverse effects. Such modifications are known in the art.

Amino Acid

Preferably the amino acid used in the invention has a water solubility of about 1.1 or less g/100 ml $H_2O$ at 25° C. Particularly preferred amino acids are tyrosine or tryptophan; the more insoluble tyrosine being preferred. Pharmaceutically acceptable derivatives of these amino acids are also included within the scope of the present invention, such as benzyl-O-octadecanoyl-L-tyrosine.

Preparation

The composition of the present invention is prepared by mixing an aqueous solution of the antigen with a solution of the amino acid in a strong aqueous acid and neutralising the mixture of solution, thereby co-precipitating the amino acid and antigen.

Typically an aqueous solution of the antigen, preferably at pH 6.3 to 7.2, is mixed with a solution of the amino acid in a strong aqueous acid. The strong acid is usually an inorganic acid, preferable hydrochloric acid. The solution of antigen used in this step typically contains up to 0.15 g/ml antigen protein. In one embodiment the solution of amino acid used is about 24% w/v.

The resulting mixture of solutions of antigen and amino acid is neutralised. It is desirable that, at no time, or at least no prolonged time, during the neutralisation does the pH of the solution deviate from equilibrium. This condition can be met by vigorous stirring of the solution and by the use only of the required amount of base, if desired. Various buffering agents such as buffered saline solution can usefully be added to the solutions of antigen to assist in pH control during mixing and neutralising stages.

A particularly useful method of carrying out the neutralisation is for separate streams of the solution of amino acid and neutralising base to be run into the solution of antigen. The rates of flow of the added solutions are controlled by pH-state, that is by equipment which regulates the flow of one or both of the solutions so that the pH of the reaction mixture remains substantially constant at a predetermined level. We have found that optimum results are usually obtained by pH control within the range 6.5 to 7.5, preferably 6.8 to 7.2, though the precise pH may vary according to the nature of the antigen.

The result of the neutralisation is the immediate precipitation of the amino acid, within and/or upon which the solution of antigen is occluded and/or adsorbed.

Cross-Flow Filtration

A method that has been useful in the fractionation of various particles is cross-flow filtration or tangential-flow filtration (TFF). Cross-flow filtration is a separation process that uses membranes to separate components in a liquid solution or suspension on the basis of size or molecule weight differences. In cross-flow filtration, the solution or suspension to be filtered is passed across the surface of the membrane in a cross-flow mode. The driving force for filtration is the transmembrane pressure. The velocity at which the filtrate is passed across the membrane surface also controls the filtration rate and helps prevent clogging of the membrane. Because cross-flow filtration recirculates retentate across the membrane surface, membrane fouling is minimized, a high filtration rate is maintained, and product recovery is enhanced.

Cross-flow filtration devices generally comprise a pump, a feed solution reservoir, a filtration module and conduits for connecting these elements. In use, the feed solution is directed from the feed solution reservoir to the filtration module while the retentate from the filtration module is recirculated from the filtration module to the feed solution reservoir until the desired volume of retentate is obtained.

The cross-flow filtration used in the present invention to separate the adsorbate comprising the modified antigen and the amino acid is preferably performed using a 5 μm pore size poly-sintered stainless steel filter maintaining pressure between 1.1 to 1.3 bar.

Closed System

A closed system is an isolated system that prevents exposure of the composition to the environment outside of the system. The composition is only exposed to the immediate environment of tubing and machine components that make up the closed system. The closed system of the present invention prevents contamination of the composition. It achieves this by ensuring that the composition is sealed off from the environment external to the system, preventing contaminants from entering the system.

Adjuvant

An adjuvant may be added to the composition produced by the method of the present invention. Preferably the adjuvant is a TH1-inducing adjuvant. A TH1-inducing adjuvant is an adjuvant that enhances the TH1 response to an antigen.

The effectiveness of an adjuvant as a TH1-inducing adjuvant may be determined by determining the profile of antibodies directed against an antigen resulting from administration of this antigen in vaccines which are also comprised of the various adjuvants.

Preferably the adjuvant is a modified lipopolysaccharide. As described in U.S. Pat. No. 4,912,094 enterobacterial lipopolysaccharides (LPS) is a powerful immunostimulant. However, it can also illicit harmful and sometimes fatal responses. It is now known that the endotoxic activities associated with LPS result from its lipid A component. Accordingly, the present invention more preferably uses a detoxified derivative of lipid A. Ribi ImmunoChem produced a derivative of lipid A originally known as refined detoxified endotoxin (RDE) but which has become known as monophosphoryl lipid A (MPL). As described in U.S. Pat. No. 4,912,094, MPL is produced by refluxing LPS or lipid A obtained from heptoseless mutants of gram negative bacteria (e.g. *Salmonella* sp.) in mineral acid solutions of moderate strength (e.g. 0.1N HCl) for a period of around 30 minutes. This treatment results in loss of the phosphate moiety at position 1 of the reducing-end glucosamine. In addition the core carbohydrate is removed from the 6' position of the non-reducing glucosamine during this treatment.

Preferably, however, a modified LPS or lipid A is used in which the detoxified lipid A retains the core moiety attached to the 6' position of non-reducing glucosamine. Such derivatives of LPS and lipid A are also described in U.S. Pat. No. 4,912,094. In more detail, U.S. Pat. No. 4,912,094 discloses a modified lipopolysaccharide which is obtained by the method of selectively removing only the β-hydroxymyristic acyl residue of lipopolysaccharide that is ester-linked to the reducing-end glucosamine at position 3' of said lipopolysaccharide, which comprises subjecting said lipopolysaccharide to alkaline hydrolysis. Such de-O-acylated monophosphoryl lipid A (MPL), diphosphoryl lipid A (DPL) and LPS may be used in the present invention. Thus in a preferred embodiment, the present invention uses MPL, DPL or LPS in which the position 3' of the reducing end glucosamine is de-O-acylated. These compounds are known as 3-DMPL, 3-DDPL and 3-DLPS respectively.

In U.S. Pat. No. 4,987,237 derivatives of MPL having the formula:

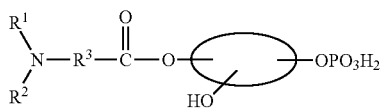

are described, and wherein $R^1$ and $R^2$ are H, $R^3$ is straight or branched chain hydrocarbon composed of C, H and optionally O, N and S, which if more than one atom may be the same or different, wherein the total number of C atoms does not exceed 60, and the circle represents an MPL nucleus.

Alternatively the MPL derivative has the formula

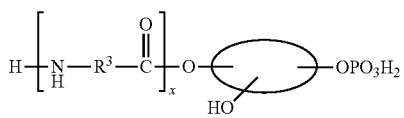

wherein the segment of the derivative represented by

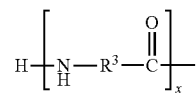

contains 2-60 C atoms and wherein $R^3$ is straight or branched chain hydrocarbon composed of C, H and optionally O, N and S, which if more than one atom may be the same or different, and x is a minimum of 1 and can be any whole number such that the total number of C atoms in all x segments does not exceed 60, and wherein the chemical structure of each $R^3$ may be the same or different in each such segment and wherein the circle represents an MPL nucleus.

All such derivatives or salts of LPS or lipid A which are or become available may be used in the present invention. Preferably derivatives and salts are ones which are pharmaceutically acceptable.

Dosage and Administration of Compositions

The compositions produced by the present invention may be administered to a subject in a manner compatible with the dosage formulation, and in such amount as will be prophylactically and/or therapeutically effective. The quantity to be administered, which is generally in the range of 5 μg to 250 μg of antigen per dose, depends on the subject to be treated, capacity of the subject's immune system to synthesize antibodies, and the degree of protection desired. A preferable range is from about 20 μg to about 40 μg per dose.

A suitable dose size is about 0.5 ml. Accordingly, a dose for sub-cutaneous injection, for example, would comprise 0.5 ml containing 20 μg of immunogen in admixture with 0.5% adjuvant.

Precise amounts of active ingredient required to be administered may depend on the judgement of the practitioner and may be peculiar to each subject.

The composition may be given in a single dose schedule, or preferably in a multiple dose schedule. A multiple dose schedule is one in which a primary course of vaccination may be with 1-20 separate doses, followed by other doses given at subsequent time intervals required to maintain and or reinforce the immune response, for example, at 1 to 4 months for a second dose, and if needed, a subsequent dose(s) after several months. The dosage regimen will also, at least in part, be determined by the need of the individual and be dependent upon the judgement of the practitioner.

In addition, the composition containing the antigen(s) may be administered in conjunction with other immunoregulatory agents, for example, immunoglobulins.

Figure 1:
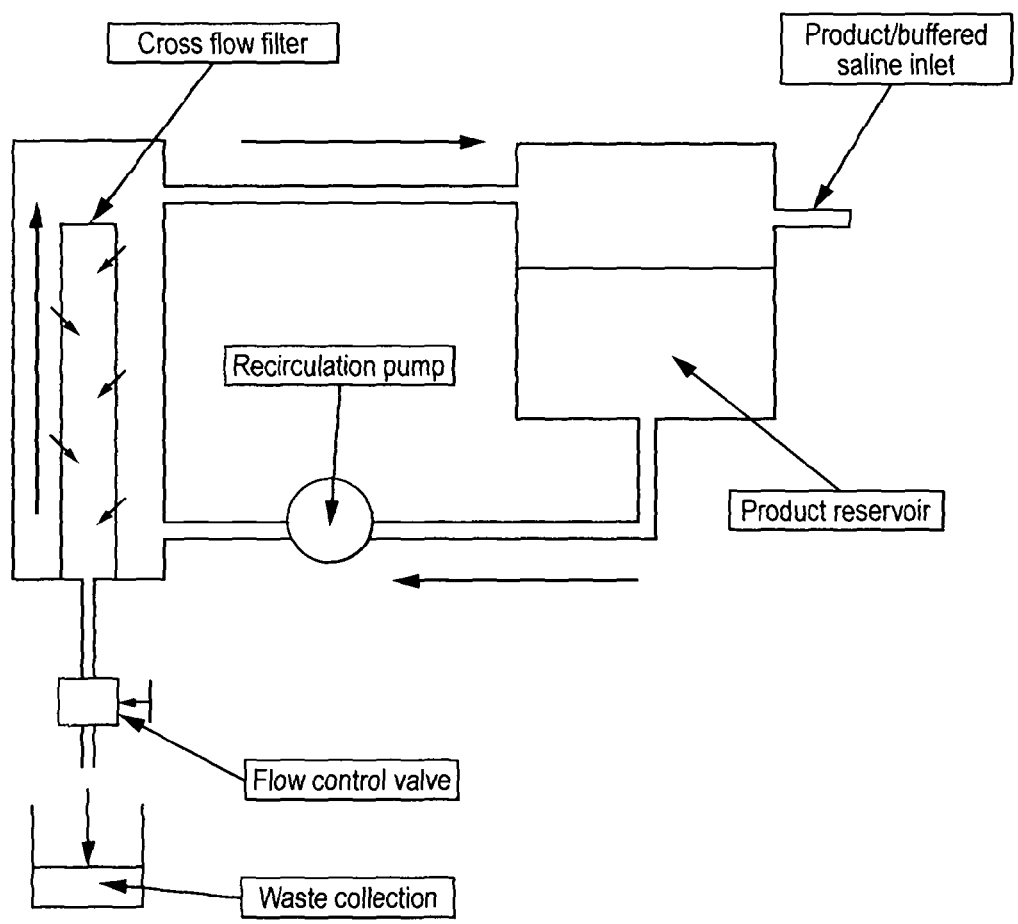
FIG. 1. Schematic representation of the cross-flow filration system used to separate the amino acid adsorbate FIG. 2. Schematic poly-sintered stainless steel filter used in cross-flow filtration; Figure shows filter housing (A) and assembly in-situ (B)
Figure 2:
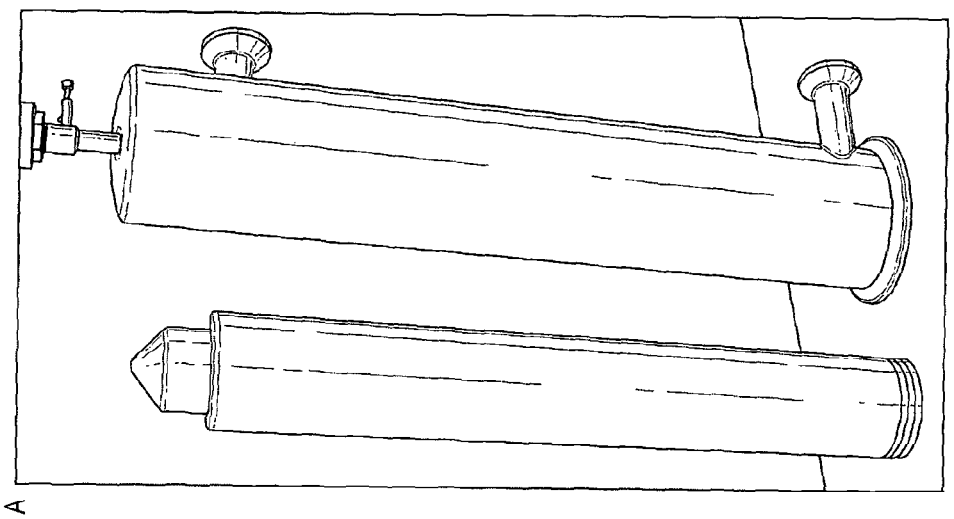
Figure 2:
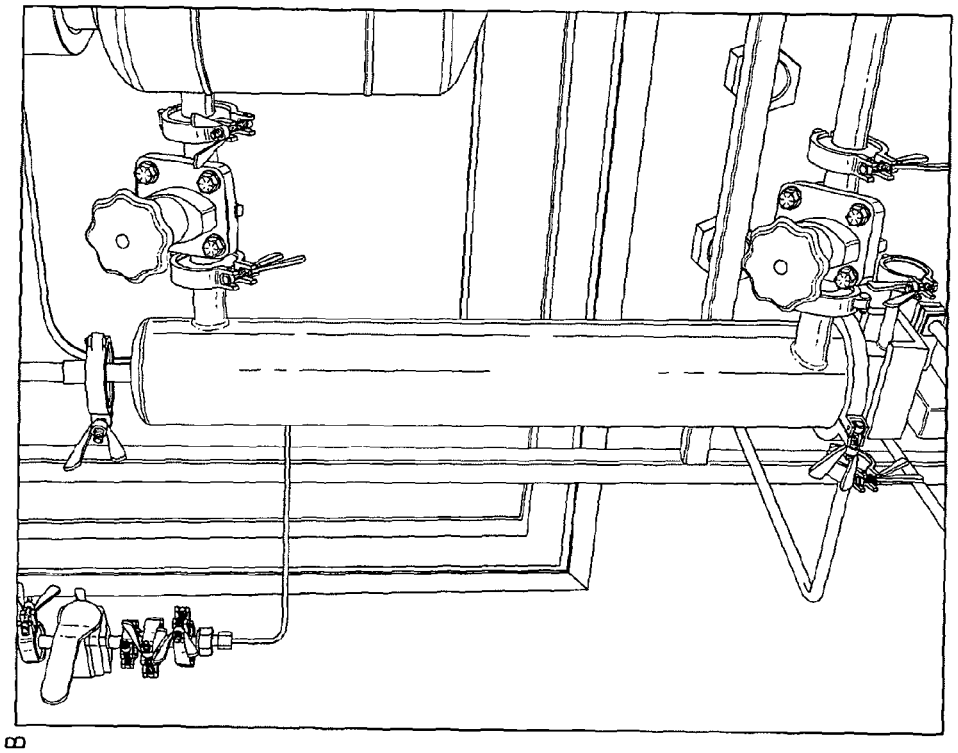
Figure 3:
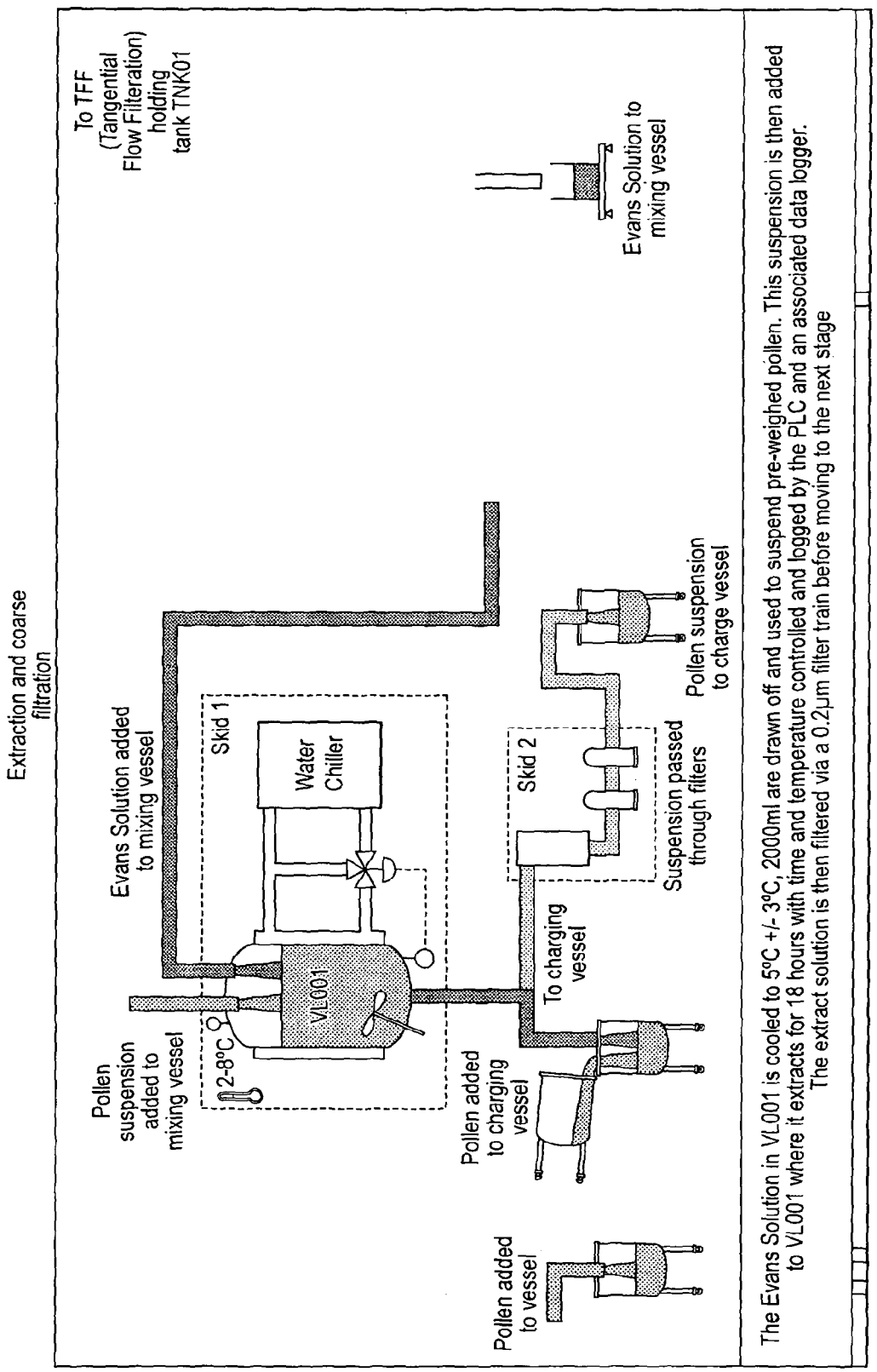
FIG. 3. Schematic of the extraction of pollen antigens into extract solution. The Evans Solution in VL001 is cooled to 5° C.+/−3° C., 2000 ml are drawn off and used to suspend pre-weighed pollen. This suspension is then added to VL001 where it extracts for 18 hours with time and temperature controlled and logged by the PLC and an associated data logger. The extract solution is then filtered via a 0.2 μm filter train before moving to the next stage.
Figure 4:
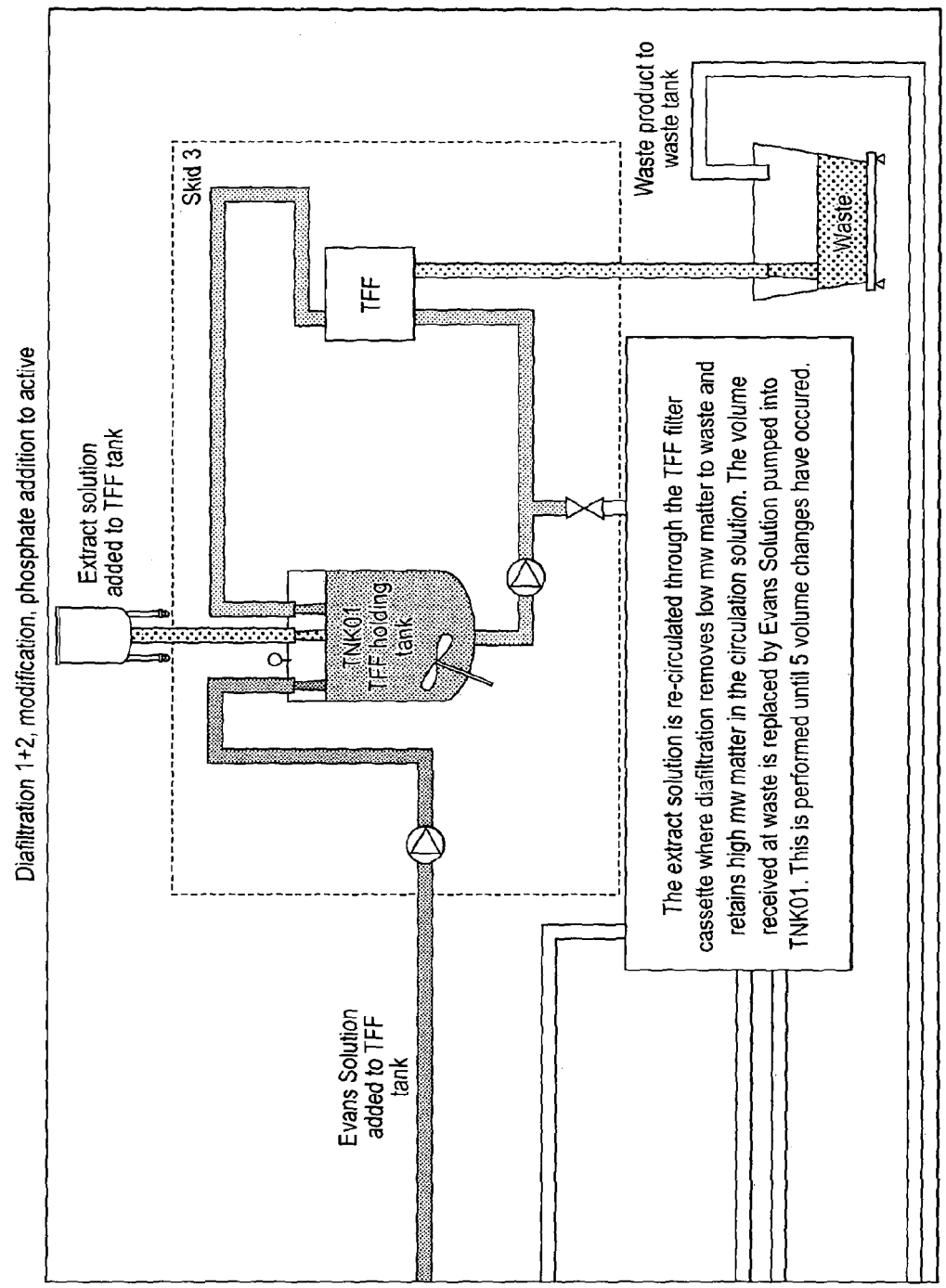
FIG. 4. Schematic of the cross-flow filtration to isolate the retenate comprising the pollen antigen. The extract solution is re-circulated through the TFF filter cassette where diafiltration removes low mw matter to waste and retains high mw matter in the circulating solution. The volume received at waste is replaced by Evans Solution pumped into TNK01. This is performed until 5 volume changes have occurred FIG. 5. Schematic of the modification of the pollen antigens with glutaraldehyde. Pre-weighed glutaraldehyde is added to the diafiltered solution. Once added the solution is left with agitation to modify for 1-2 hours.
Figure 5:
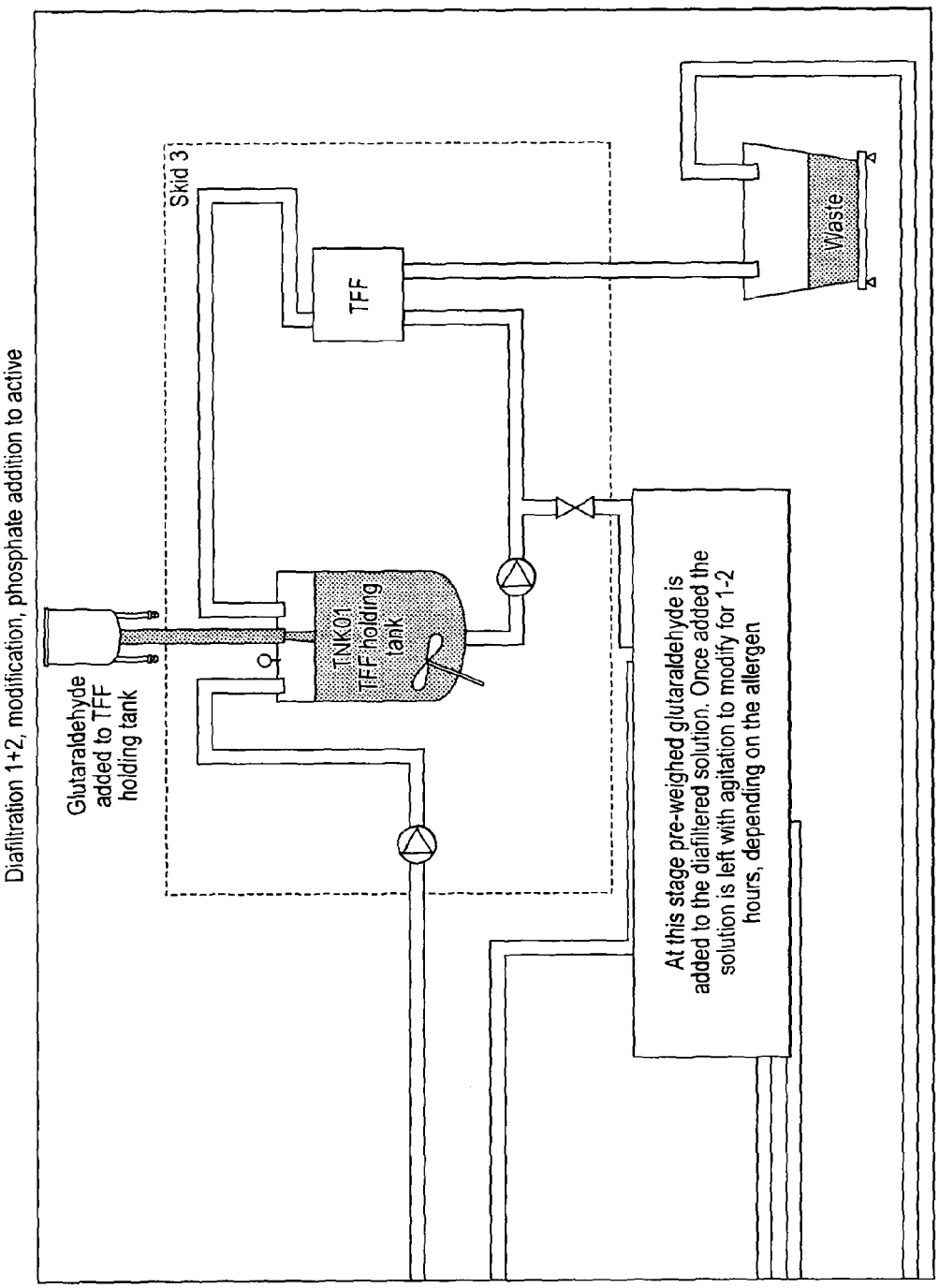
Figure 6:
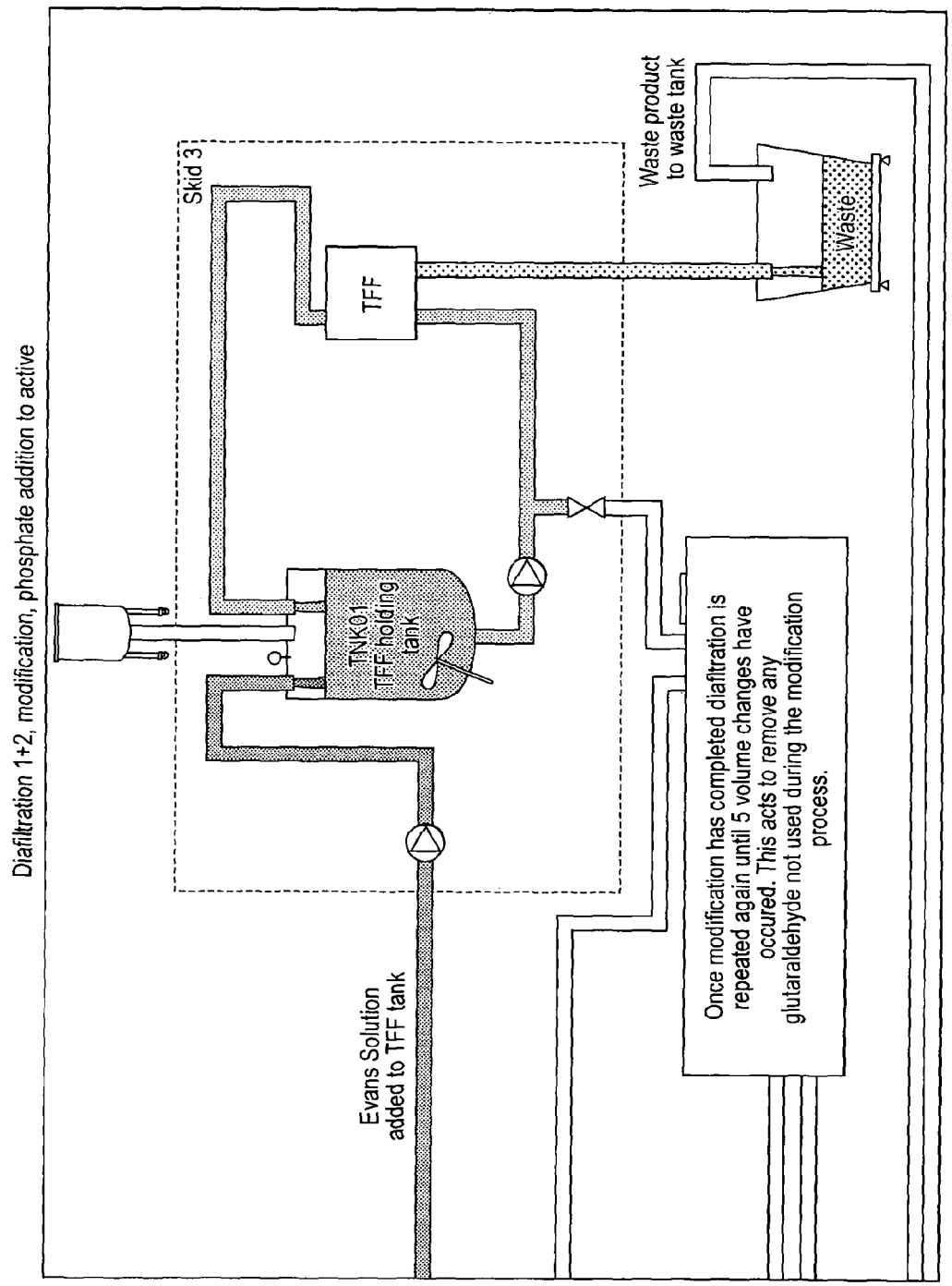
FIG. 6. Schematic of the removal of excess glutaraldehyde. Once modification has completed diafiltration is repeated again until 5 volume changes have occurred. This acts to remove any glutaraldehyde not used during the modification process.
Figure 7:
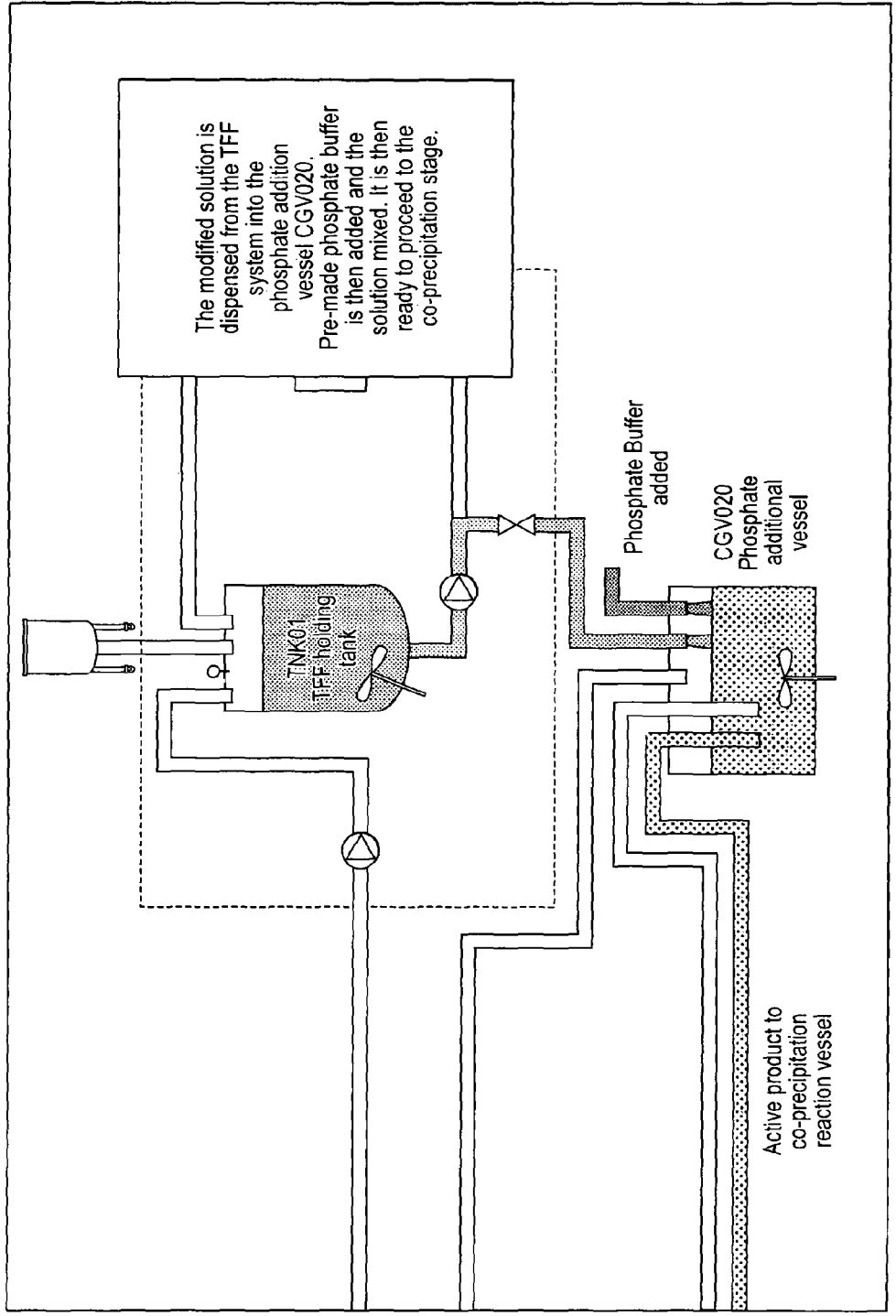
FIG. 7. Schematic showing that the modified solution is dispensed from the TFF system into the phosphate addition vessel CGV020. Pre-made phosphate buffer is then added and the solution mixed. It is then ready to proceed to the co-precipitation stage.
Figure 8:
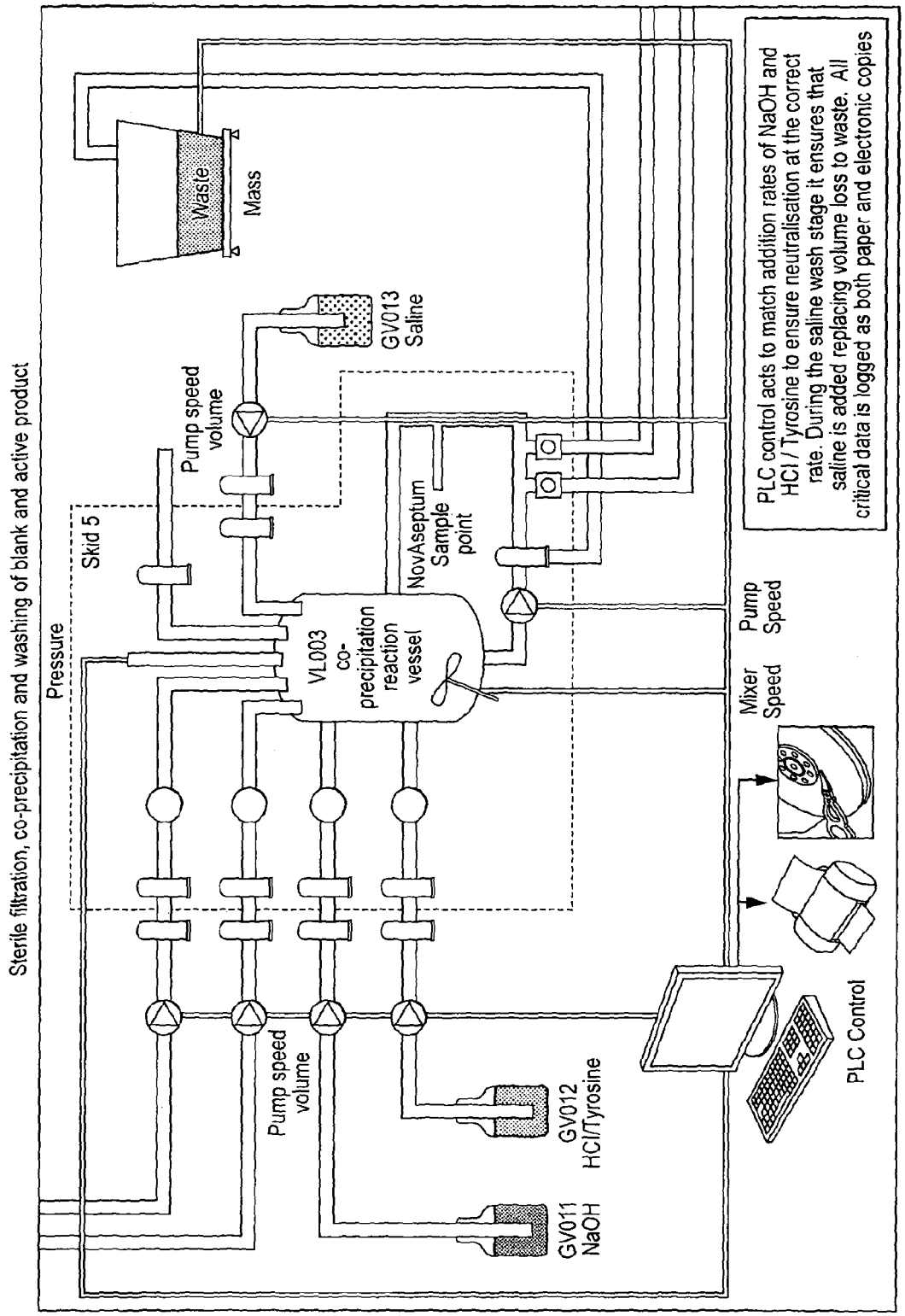
FIG. 8. Schematic showing how PLC control acts to match addition rates of NaOH and HCl/Tyrosine to ensure neutralisation at the correct rate. During the saline wash stage it ensures that saline is added replacing volume loss to waste. All critical data is logged as both paper and electronic copies.
Figure 9:
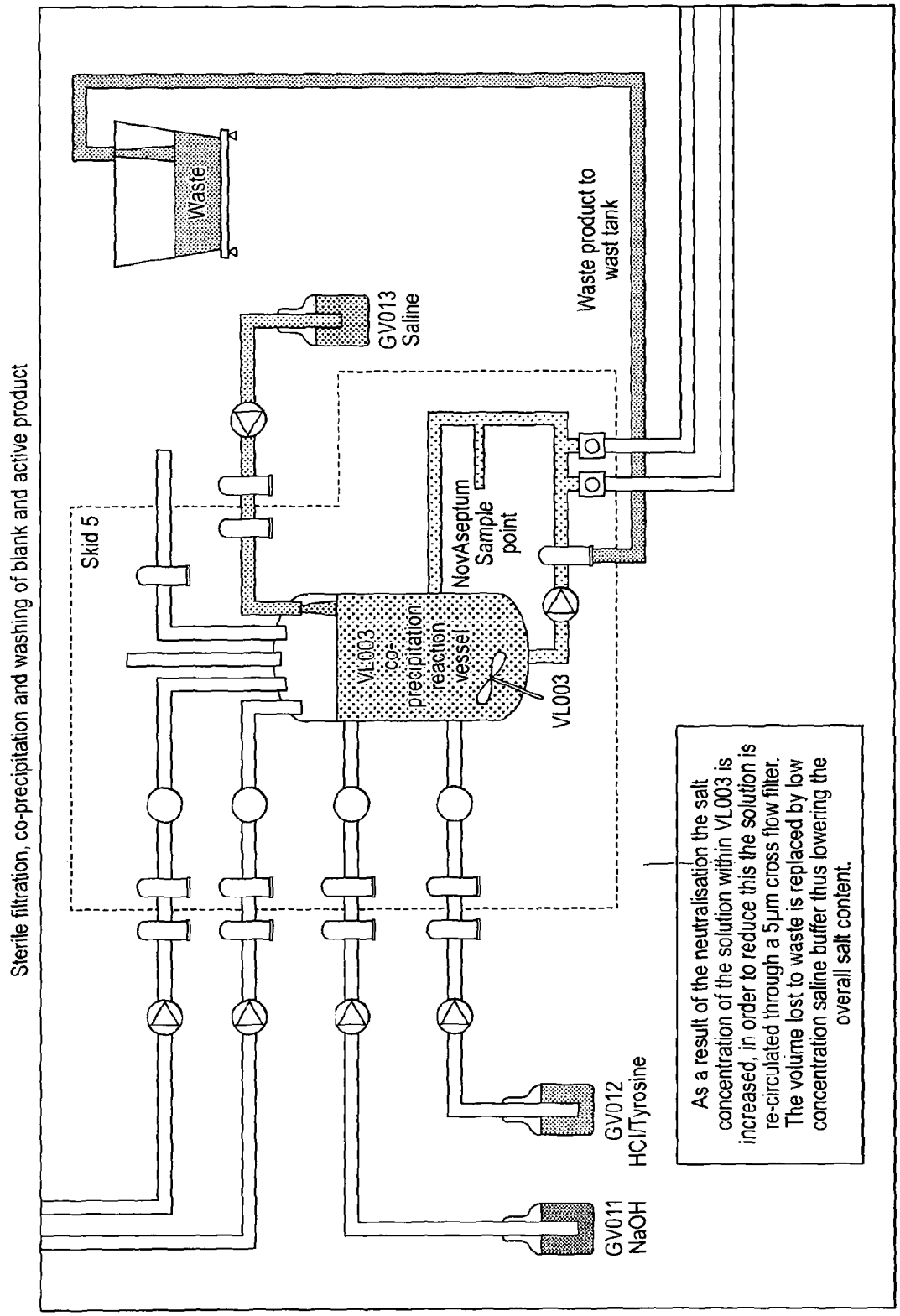
FIG. 9. Schematic showing how the salt concentration of the solution within VL003 is reduced by re-circulated through a 5 μm cross flow filter. The volume lost to waste is replaced by low concentration saline buffer thus lowering the overall salt content.
Figure 10:
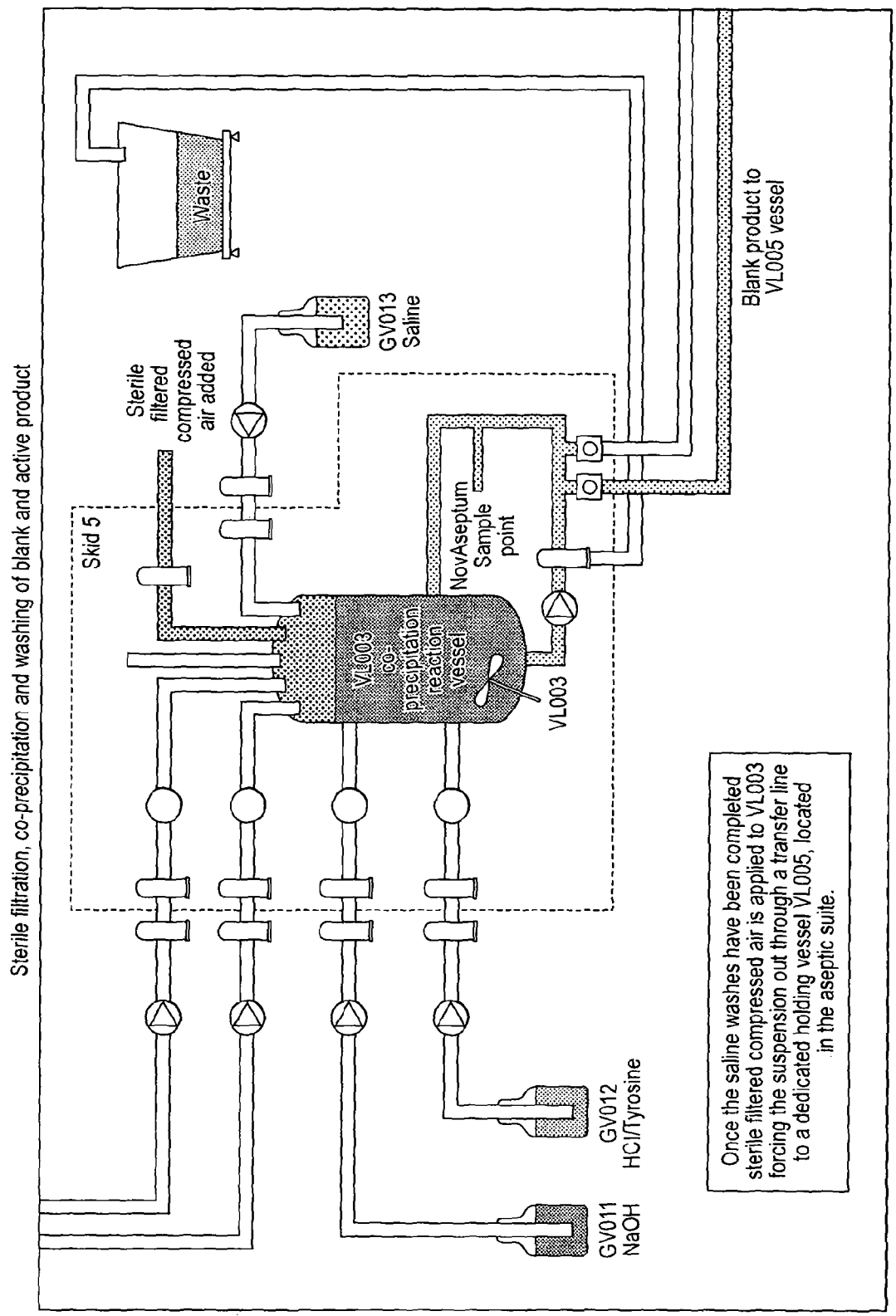
FIG. 10. Schematic showing that once the saline washes have been completed sterile filtered compressed air is applied to VL003 forcing the suspension out through a transfer line to a dedicated holding vessel VL005, located in the aseptic suite.
Figure 11:
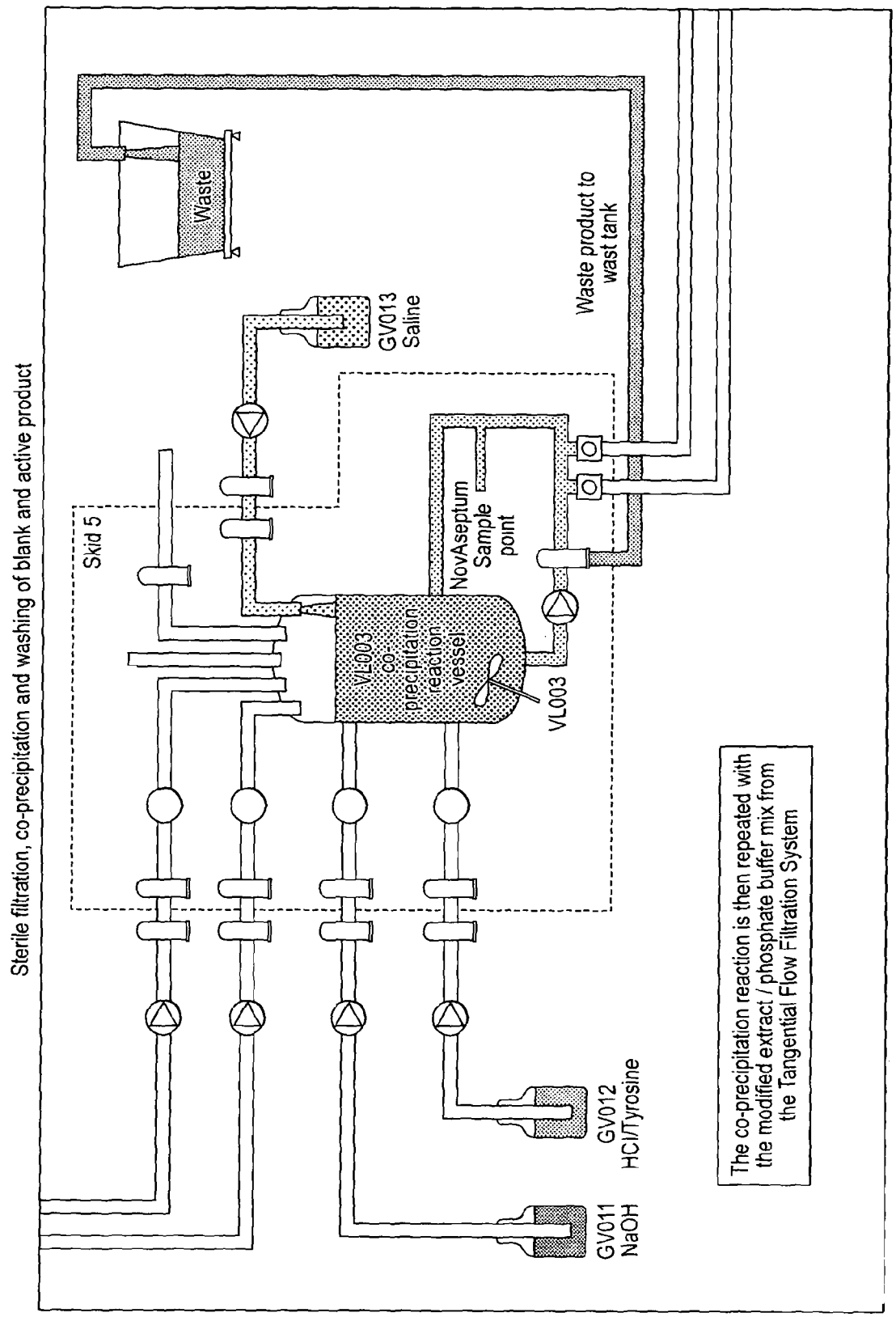
FIG. 11. Schematic showing that the co-precipitation reaction is then repeated with the modified extract/phosphate buffer mix from the Tangential Flow Filtration system FIG. 12. Schematic of the co-precipitation system showing all connections.
Figure 12:
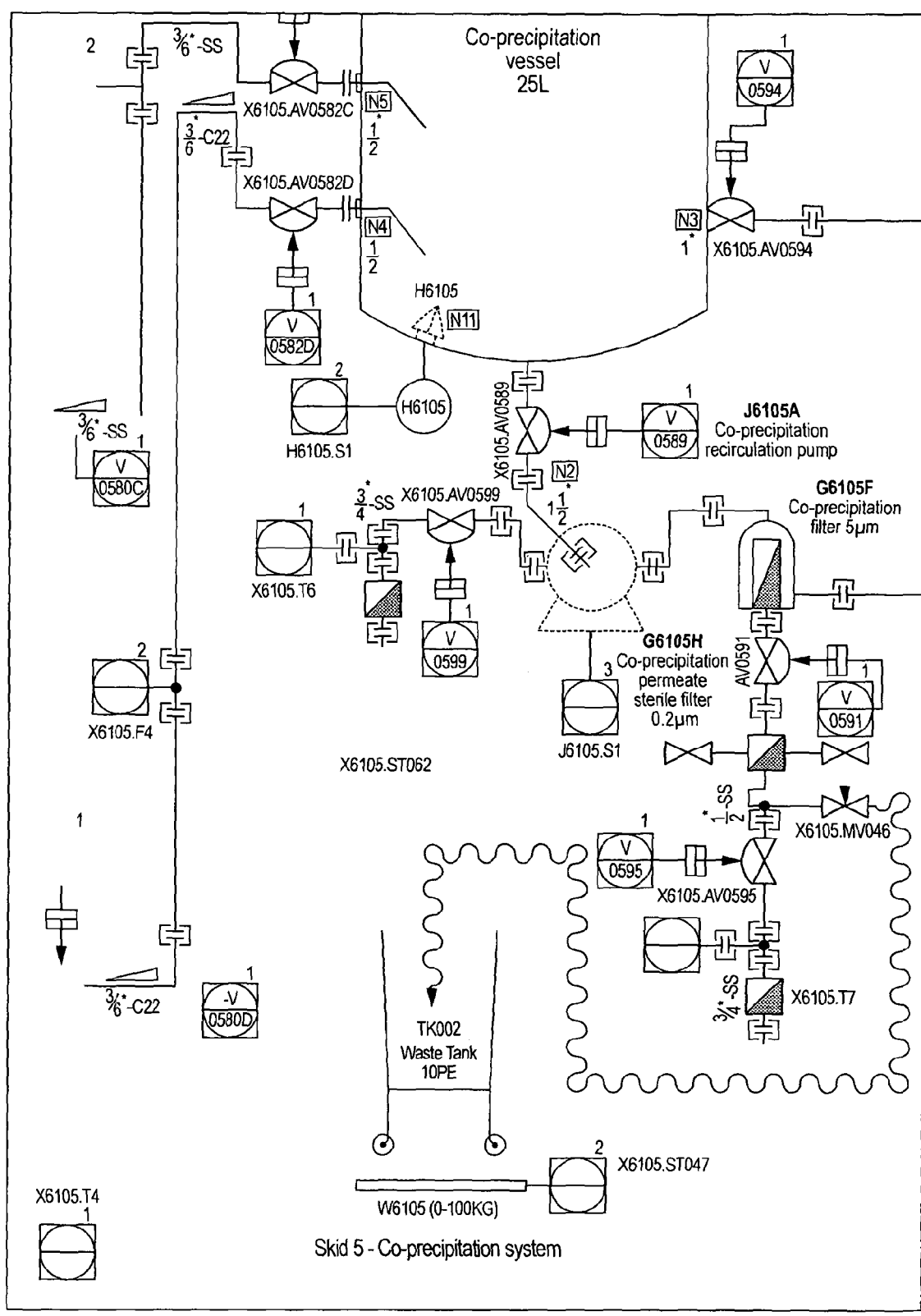
Figure 12:
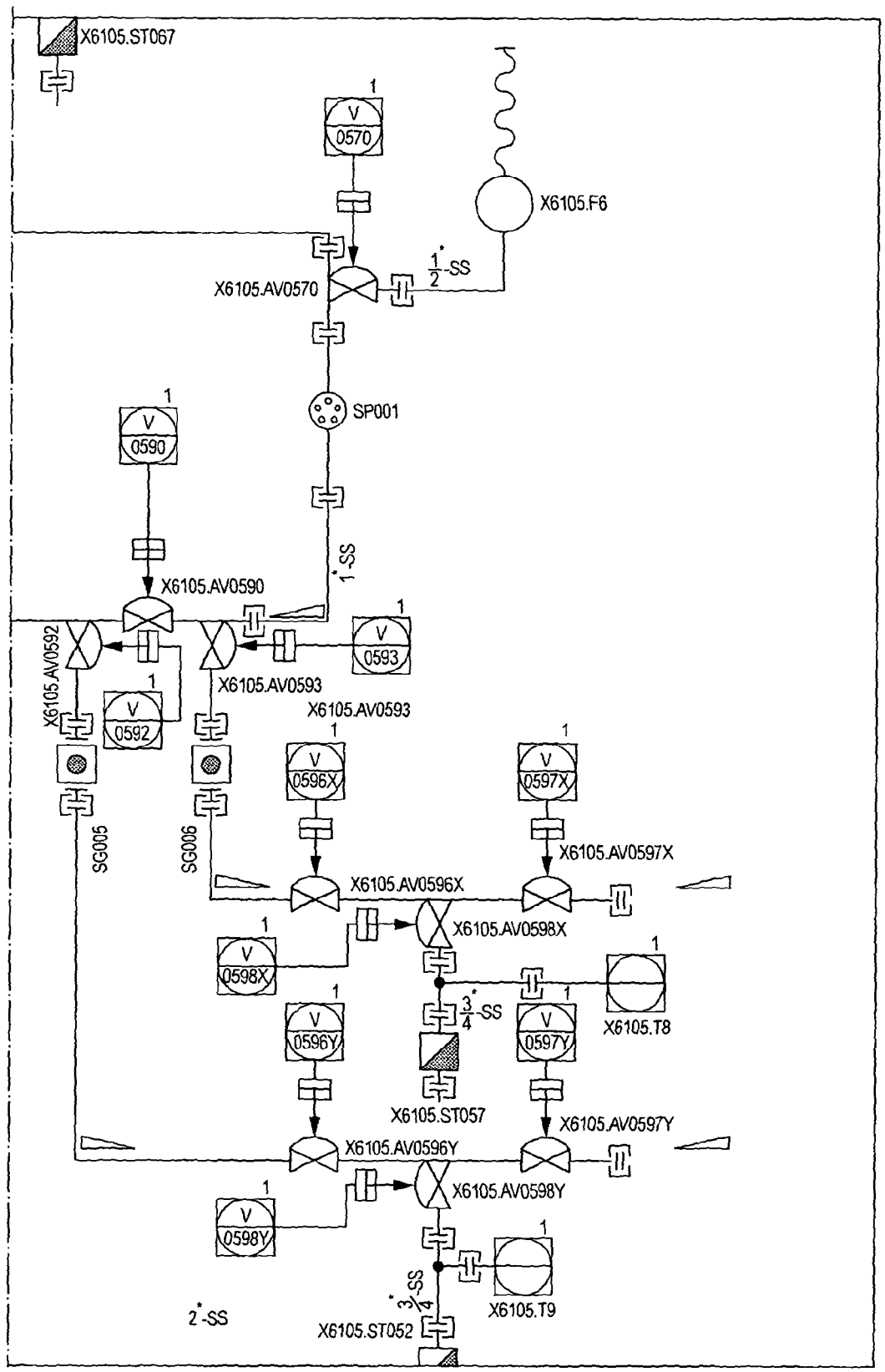
Figure 13:
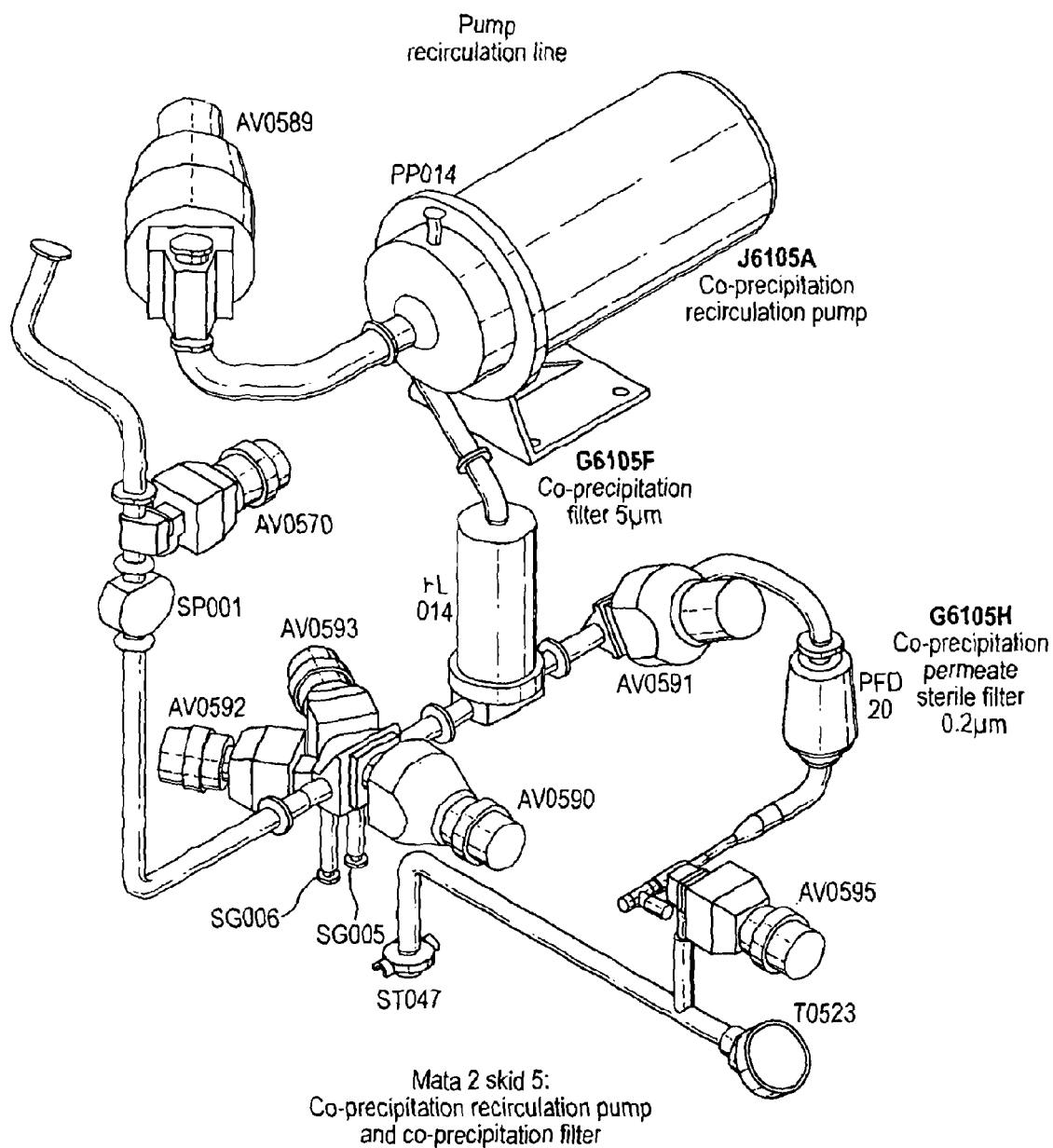
FIG. 13. Diagram at the design stage showing the linkage between the pump, cross-flow filter and the permeate sterile filter 0.2 μm through which the wash liquor is drawn during salt reduction of the co-precipitation solids.

Further preferred features and embodiments of the present invention will now be described by way of non-limiting example and with reference to the accompanying drawings in which:

EXAMPLE

Thirteen raw grass pollens (Bent pollen, Foxtail pollen, Sweet vernal pollen, False oat pollen, Brome pollen, Crested dogstail pollen, Cocksfoot pollen, Fescue pollen, Yorkshire fog pollen, Rye grass pollen, Timothy pollen, Meadow pollen and Cultivated rye pollen) are extracted in a custom stainless steel vessel with Evans solution (pH 6.5) (Sodium Chloride, Potassium Di-Hydrogen Phosphate, Disodium Phosphate Dodecahydrate, 80% w/w Liquified Phenol and Water for Injections) at 5° C. for 18 hours with agitation. The mixture is then filtered down to 0.2 μm to remove solids via a Pall filter or similar. The process controller regulates the temperature and the flow coolant to the extraction vessel. At the end of the extraction period in process testing of the filtrate is carried out to determine the effectiveness of the process. These include pH, IgE reactivity, IgG potency, allergen and Polymer profile.

The pollen extract now undergoes diafiltration by passing through a Cogent tangential flow system using a trans-membrane pressure of between 0.2-0.6 Bar for five volume changes using a 10 kDa molecular weight cut-off membrane. The retentate is dispensed to a clean sanitised vessel and a 10% glutaraldehyde solution by weight is added and modification now takes place for 2 hours to form allergoids. The benefits of this process are reduced IgE and retained IgG inducing capacity. The degree of modification varies but should be in the order of 50 to 100%.

The modified extract then undergoes a second diafiltration step through the Cogent tangential-flow system against Evans solution pH 7.0 (Sodium Chloride, Potassium Di-Hydrogen Phosphate, Disodium Phosphate Dodecahydrate, 80% w/w Liquified Phenol and Water for Injections) using a membrane with a 5 to 10 kDa molecular weight cut-off to remove excess glutaraldehyde. The final extract (Drug Substance) is submitted to a battery of Quality assurance tests including primary amine loss; protein content; IgE reactivity; IgG potency and Polymer profile.

The drug substance is sterile filtered through a 0.2 μm pore size filter into a clean pre-sanitised vessel to which further sterile filtered phosphate buffer (Sodium Dihydrogen Phosphate Dihydrate, Disodium Phosphate Dodecahydrate, Water for Injections) is added to the required concentration. 24% sterile L-tyrosine in 3.8M hydrochloric acid and 3.2M sodium hydroxide are simultaneously added to the reaction vessel fitted with a high shear stirrer and co-precipitation occurs. This process results in a high salt content which is reduced by washing the tyrosine precipitate using a Sum cross-flow poly-sintered stainless steal filter in a closed system. A 5 μm cross-flow filter is used to achieve separation and the volume lost is replaced with low concentration saline buffer, the tyrosine adsorbed allergoid is then recovered into a fresh clean pre-sterilised vessel by applying sterile compressed air to the holding vessel forcing the suspension out. Pipework for all material transfer is Clean in Place (CIP)/Steam in Place (SIP).

Following manufacture the active bulk is held in bespoke equipment and transferred to a dilution vessel for additions of tyrosine and MPL for mixing and aseptic filling into 3 ml butyl serum stoppered vials.

The exemplified method has logic control over critical aspects of the process and utilises Nova Septum sterile connections to minimise the possibility of false positive contamination results. The method has in process controls and in line testing to ensure compliance. The equipment has been designed to minimise exposure of the operatives to hazardous materials and utilises clean in place, steam in place technology to provide a fully validated clean and sterile process.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A method of preparing a composition comprising one or more antigens adsorbed to an amino acid wherein said method comprises:
   (i) mixing a solution of one or more antigens with a solution of the amino acid in an aqueous acid whilst neutralising the mixture of solutions, thereby forming an adsorbate comprising the one or more antigens and the amino acid;
   (ii) separating the adsorbate into a buffer by cross-flow filtration thereby forming said composition; and
   (iii) recovering said composition;
   wherein steps (i) to (iii) are performed in a sterile environment and within a clean in place (CIP) and steam in place (SIP) closed system.

2. The method according to claim 1, wherein the amino acid is tyrosine.

3. The method according claim 1, wherein the one or more antigens are modified with glutaraldehyde.

4. The method according to claim 1, wherein the one or more antigens are derived from pollen.

5. The method according to claim 1 comprising preparing a composition comprising one or more pollen antigens modified with glutaraldehyde and adsorbed to tyrosine wherein said method comprises:
   (i) modifying the one or more pollen antigens with glutaraldehyde;
   (ii) removing excess glutaraldehyde using cross-flow filtration to form a modified pollen solution;
   (iii) mixing the modified pollen solution with a solution of the tyrosine in an aqueous acid whilst neutralising the mixture of solutions, thereby forming an adsorbate comprising the modified pollen and the tyrosine;
   (iv) separating the adsorbate into a buffer by cross-flow filtration thereby forming said composition; and
   (v) recovering said composition;
   wherein steps (iii) to (v) are performed in a sterile environment and within a clean in place (CIP) and steam in place (SIP) closed system.

6. The method according to claim 1 comprising preparing a composition comprising one or more pollen antigens modified with glutaraldehyde and adsorbed to tyrosine wherein said method comprises:
   (i) extracting the one or more pollen antigens into solution to form a pollen extract solution;
   (ii) filtering the pollen extract solution to remove solids;
   (iii) performing cross-flow filtration and isolating the retentate comprising the pollen antigen;
   (iv) modifying the one or more pollen antigens with glutaraldehyde;
   (v) removing excess glutaraldehyde using cross-flow filtration to form a modified pollen solution;
   (vi) sterile filtering the modified pollen solution;
   (vii) mixing the modified pollen solution with a solution of tyrosine in an aqueous acid whilst neutralising the mixture of solutions, thereby forming an adsorbate comprising the modified pollen and the tyrosine;
   (viii) separating the adsorbate into a buffer by cross-flow filtration thereby forming said composition; and
   (ix) recovering said composition;
   wherein steps (vii) to (ix) are performed in a sterile environment and within a clean in place (CIP) and steam in place (SIP) closed system.

7. The method according to claim 1, wherein the composition comprises the pollen antigens: Bent pollen, Foxtail pollen, Sweet vernal pollen, False oat pollen, Brome pollen, Crested dogstail pollen, Cocksfoot pollen, Fescue pollen, Yorkshire fog pollen, Rye grass pollen, Timothy pollen, Meadow pollen and Cultivated rye pollen.

8. The method according to claim 6, wherein extraction step (i) is performed using a phenolic buffered solution at about 2 to about 8° C. for about 18 hours.

9. The method according to claim 5, wherein removing the excess glutaraldehyde using cross-flow filtration is performed using a membrane with a 5 to 10 kDa molecular weight cut-off.

10. The method according to claim 1, wherein separating the adsorbate comprising the antigen and the amino acid using cross-flow filtration is performed using a poly-sintered stainless steel filter.

11. The method according to claim 10, wherein the poly-sinstered stainless steel filter is a 5 μm pore size filter.

12. The method according to claim 1, wherein the adsorbate comprising the antigen and the amino acid is formed by mixing the antigen with amino acid in HCl having a molarity of about 3.8M whilst neutralising the mixture with NaOH having a molarity of about 3.2 M.

13. The method according to claim 1, wherein said composition is diluted to the desired concentration for parental use.

14. The method according to claim 1, wherein an adjuvant is added to said composition.

15. The method according to claim 14, wherein the adjuvant is MPL, 3-DMPL or a derivative or salt thereof.

16. The method according to claim 1, wherein the amino acid is tyrosine and the one or more antigens are derived from pollen.

17. The method according to claim 16, wherein the one or more antigens are modified with glutaraldehyde.

* * * * *